United States Patent
Ching et al.

(10) Patent No.: US 10,182,796 B2
(45) Date of Patent: Jan. 22, 2019

(54) SPECIMEN COLLECTION DEVICE AND KIT

(71) Applicant: Eve Medical Inc., Toronto, Ontario (CA)

(72) Inventors: Victoria Jessica Ching, Toronto (CA); Evan Moses, Toronto (CA); Gilad Shoham, Toronto (CA)

(73) Assignee: EVE MEDICAL INC., Toronto, ON (CA)

( * ) Notice: Subject to any disclaimer, the term of this patent is extended or adjusted under 35 U.S.C. 154(b) by 647 days.

(21) Appl. No.: 14/647,714

(22) PCT Filed: Nov. 27, 2013

(86) PCT No.: PCT/CA2013/000991
§ 371 (c)(1),
(2) Date: May 27, 2015

(87) PCT Pub. No.: WO2014/082159
PCT Pub. Date: Jun. 5, 2014

(65) Prior Publication Data
US 2015/0297196 A1 Oct. 22, 2015

Related U.S. Application Data

(60) Provisional application No. 61/732,148, filed on Nov. 30, 2012.

(51) Int. Cl.
*A61B 10/02* (2006.01)
*A61B 10/00* (2006.01)
*A61B 50/33* (2016.01)

(52) U.S. Cl.
CPC .......... *A61B 10/02* (2013.01); *A61B 10/0045* (2013.01); *A61B 10/0096* (2013.01);
(Continued)

(58) Field of Classification Search
CPC . A61B 10/02; A61B 10/0045; A61B 10/0096; A61B 50/33
(Continued)

(56) References Cited

U.S. PATENT DOCUMENTS

| 2,096,162 A | 10/1936 | Daley |
| 3,554,185 A | 1/1971 | Kohl |

(Continued)

FOREIGN PATENT DOCUMENTS

| CN | 101243982 | 8/2008 |
| CN | 201481458 | 5/2010 |

(Continued)

OTHER PUBLICATIONS

International Search Report in PCT/CA2013/000991 dated Mar. 24, 2014.
Written Opinion in PCT/CA2013/000991 dated Mar. 24, 2014.

*Primary Examiner* — King M Chu
(74) *Attorney, Agent, or Firm* — Hill & Schumacher

(57) ABSTRACT

Devices, and methods of use thereof, are provided for the collection of a biological sample during insertion into a human orifice. The device may include a body piece, an insertion piece extending from one end of the body piece, and a handle connected to the other end of the body piece. Upon rotation of the handle, a shaft housed within the body piece, with a collection end at a distal portion thereof, is extended from a retracted position to an extended position, such that the collection end exits an opening within the insertion piece. The angle of the body piece relative to the insertion piece may be configured for self-sampling of a vaginal sample in a seated position. The collection end may be a swab with a plurality of pinwheeling fins having leading edge oriented to collect the biological sample when the shaft is rotated in a given direction.

30 Claims, 15 Drawing Sheets

(52) U.S. Cl.
CPC ...... *A61B 50/33* (2016.02); *A61B 2010/0074* (2013.01); *A61B 2010/0216* (2013.01)

(58) Field of Classification Search
USPC ................................ 206/223; 600/569, 572
See application file for complete search history.

(56) References Cited

U.S. PATENT DOCUMENTS

| | | |
|---|---|---|
| 3,961,620 A | 6/1976 | Schack et al. |
| 4,157,709 A | 6/1979 | Schuster et al. |
| 4,227,537 A | 10/1980 | Suciu et al. |
| 4,318,414 A | 3/1982 | Schuster et al. |
| 4,628,941 A | 12/1986 | Kosasky |
| 5,387,205 A | 2/1995 | Cummins |
| 5,462,063 A | 10/1995 | Kist et al. |
| 5,980,542 A | 11/1999 | Saldivar |
| 6,030,397 A | 2/2000 | Monetti et al. |
| 6,193,674 B1 | 2/2001 | Zwart |
| 6,302,853 B1 | 10/2001 | Sak |
| 6,352,513 B1 | 3/2002 | Anderson et al. |
| 6,475,165 B1 | 11/2002 | Fournier |
| 7,947,057 B2 | 5/2011 | Schraga |
| 2004/0260201 A1 | 12/2004 | Mueller, Jr. |
| 2005/0131314 A1* | 6/2005 | Hird ................ C12Q 1/04 600/572 |
| 2005/0277846 A1* | 12/2005 | Chou ............ A61B 10/0291 600/569 |
| 2005/0277847 A1 | 12/2005 | Belinson |
| 2006/0189893 A1* | 8/2006 | Maltzman ........ A61B 10/0045 600/569 |
| 2007/0073186 A1 | 3/2007 | Decker et al. |
| 2007/0270713 A1 | 11/2007 | Ng |
| 2008/0262384 A1 | 10/2008 | Wiederkehr et al. |
| 2009/0275859 A1* | 11/2009 | Kim ................ A61B 10/0291 600/569 |
| 2010/0312198 A1 | 12/2010 | Guidi |
| 2011/0087133 A1 | 4/2011 | Ching et al. |
| 2012/0296355 A1 | 11/2012 | Burres |
| 2013/0066233 A1 | 3/2013 | Klein |
| 2013/0338533 A1 | 12/2013 | Olsen |

FOREIGN PATENT DOCUMENTS

| | | |
|---|---|---|
| WO | 9622053 | 7/1996 |
| WO | 0009984 | 2/2000 |
| WO | 0197693 | 12/2001 |
| WO | 2011021931 | 2/2011 |
| WO | 2013012256 | 1/2013 |

\* cited by examiner

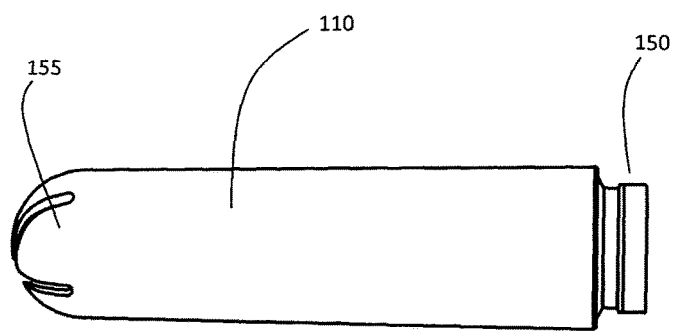
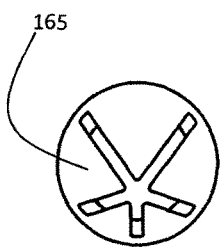
Figure 5a
Figure 5b
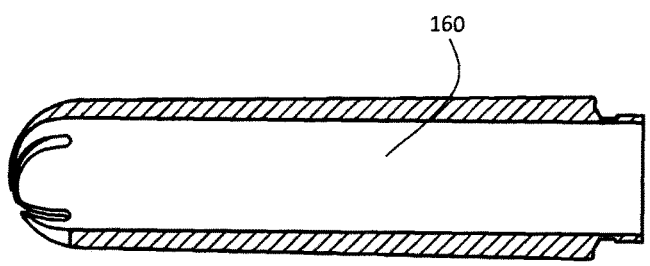
Figure 5c

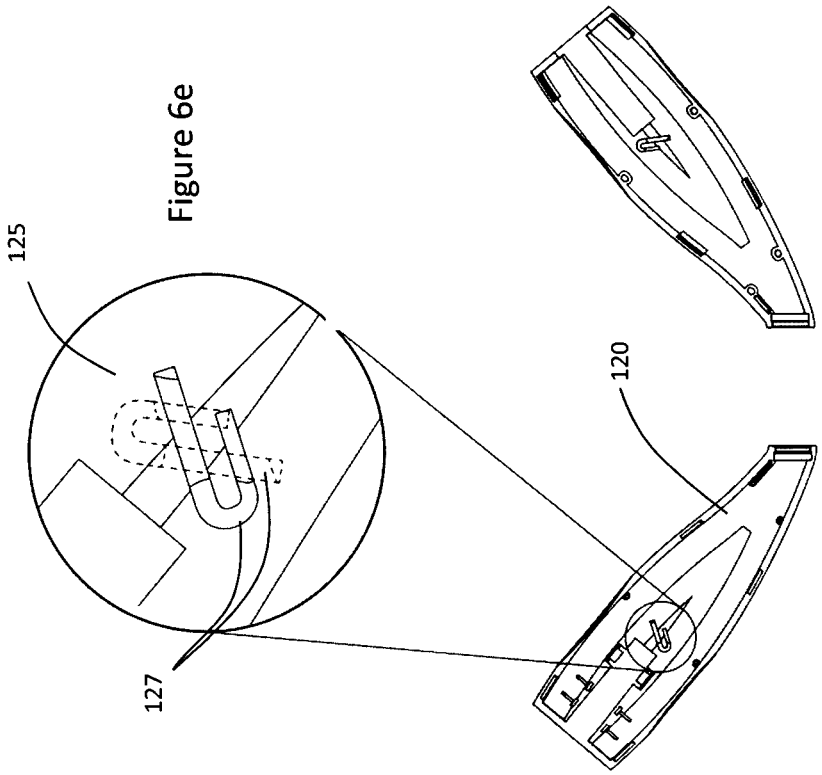
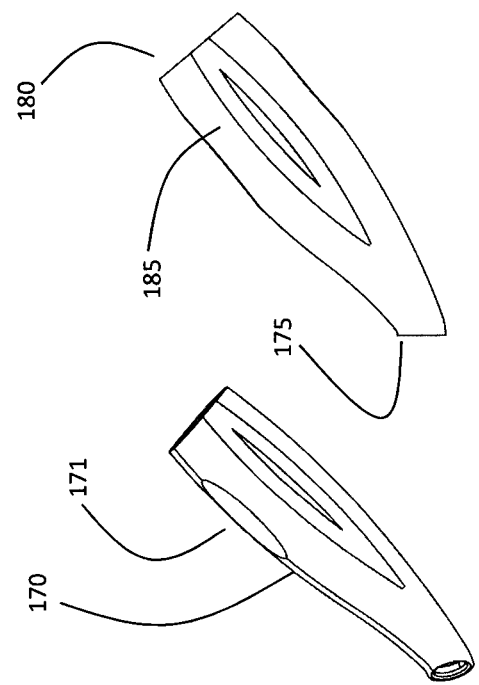

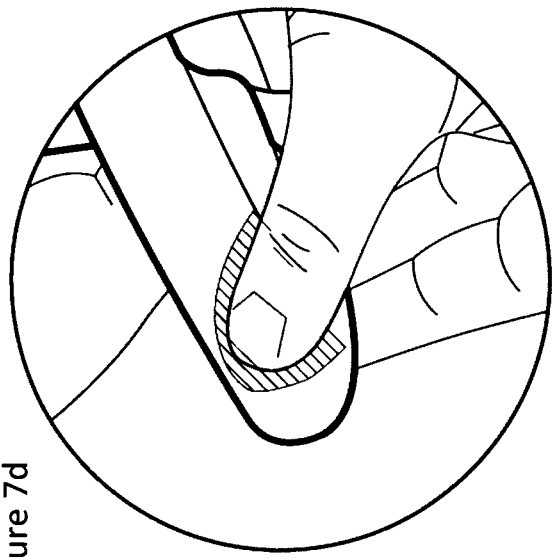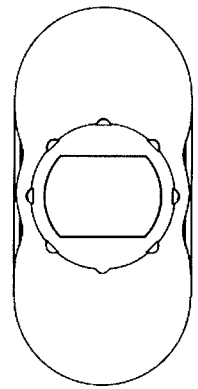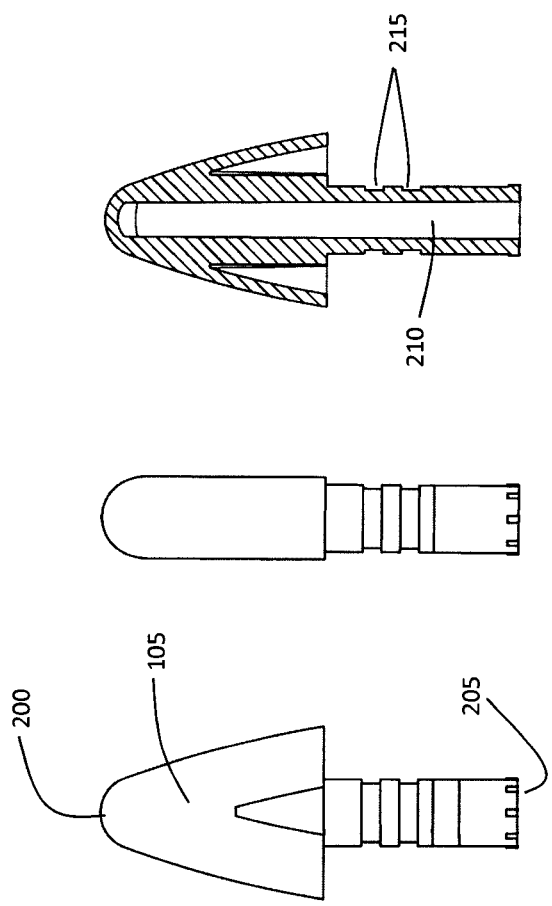

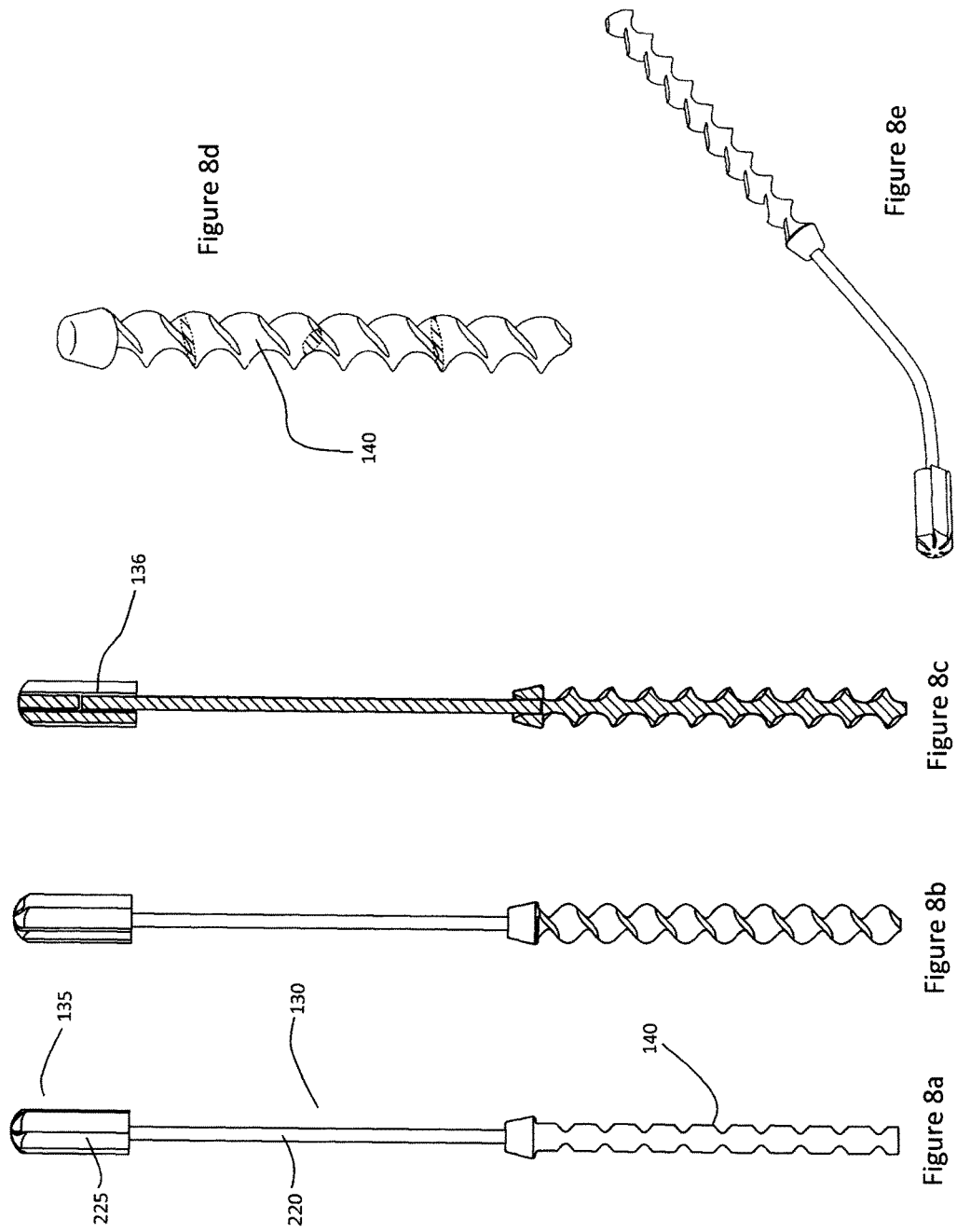

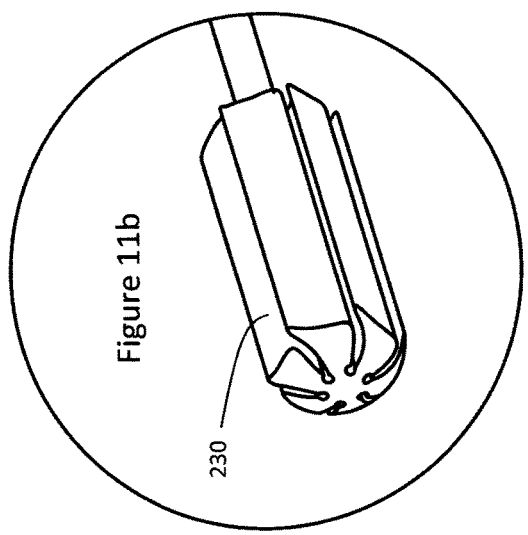
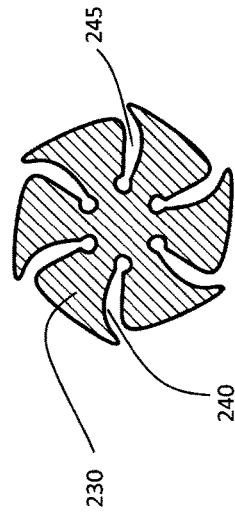
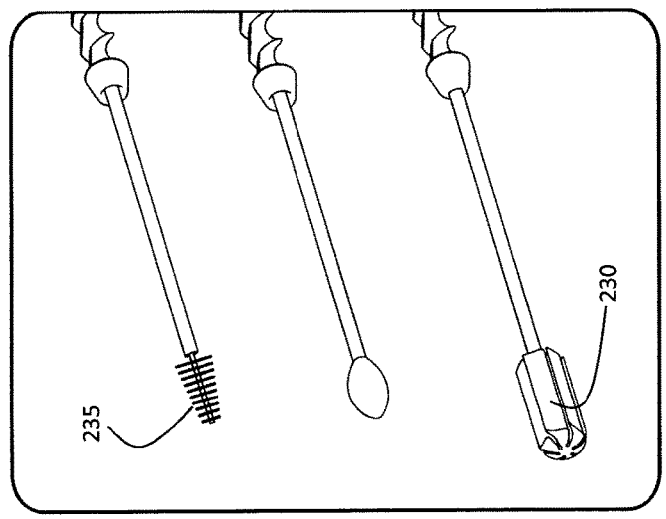

SPECIMEN COLLECTION DEVICE AND KIT

CROSS-REFERENCE TO RELATED APPLICATION

This application is a National Phase application claiming the benefit of the international PCT Patent Application No. PCT/CA2013/000991, filed on Nov. 27, 2013, in English, which claims priority to U.S. Provisional Application No. 61/732,148, titled "SPECIMEN COLLECTION DEVICE AND KIT" and filed on Nov. 30, 2012, the entire contents of which are incorporated herein by reference.

BACKGROUND

This present disclosure relates to specimen collection devices and kits that for the collection of biological samples.

Papanicolau tests ("pap tests") are still currently the primary method of screening for cervical cancer in women. Recently, however, molecular diagnostic tests for human papillomavirus (HPV), the virus that causes cervical cancer, have become a viable alternative. Because HPV diagnostics are testing for viral DNA, as opposed to the pap test which is a cytology test performed on cells, the requirements of sample collection for the two tests are different.

The pap test requires that cells be collected from the transformation zone of the cervix. This procedure requires trained personnel with a line of sight to the cervix. Many view this process as invasive, and this coupled with other factors, such as inconvenience, or lack of access, can lead to irregular screening or complete avoidance. The avoidance of screening by many women is one of the limiting factors on the greater efficacy of the pap test. Pap tests are also relatively resource-intensive and women in rural and underdeveloped locales do not always have access to the facilities or medical staff required.

With the HPV test, it becomes technically possible for patients to collect their own sample. The HPV virus can be detected in vaginal fluid and in biological material sloughed off from the cervix. Clinical studies have shown that the quality of samples collected by patients themselves can be comparable to physician collected samples, potentially allowing patients to screen themselves. A repeatable and reliable method for women to collect their own samples from near the cervix would be potentially beneficial as it may reduce the barriers that inhibit adequate screening.

SUMMARY

Devices, and methods of use thereof, are provided for the collection of a biological sample during insertion into a human orifice. The device may include a body piece, an insertion piece extending from one end of the body piece, and a handle connected to the other end of the body piece. Upon rotation of the handle, a shaft housed within the body piece, with a collection end at a distal portion thereof, is extended from a retracted position to an extended position, such that the collection end exits an opening within the insertion piece. The angle of the body piece relative to the insertion piece may be configured for self-sampling of a vaginal sample in a seated position. The collection end may be a swab with a plurality of pinwheeling fins having leading edge oriented to collect the biological sample when the shaft is rotated in a given direction.

Accordingly, in one aspect, there is provided a device for collection of a biological sample during insertion into a human orifice, the device comprising:

a rotatable handle;
a body piece attached to the handle;
an insertion piece attached to the body piece opposite the handle and extending therefrom to a tip end having an opening therein; wherein the handle, body piece, and insertion piece together define an interior region;
a threading mechanism fixed to an inner wall of the body piece;
a flexible shaft received within a sleeve defined by said handle, wherein the flexible shaft extends within the body piece and the insertion piece from the sleeve when the shaft is in a retracted position, the shaft having a collection end at a distal portion thereof and a threaded segment configured to engage the threading mechanism, the shaft being movable from the retracted position wherein the collection end is enclosed within the insertion piece to an extended position wherein the collection end exits the opening in the insertion piece; and
wherein the sleeve contacts the shaft upon rotation of the handle such that the sleeve and shaft rotate concomitantly, and wherein the threaded segment engages the threading mechanism during rotation of the handle such that the rotation of the shaft is translated into longitudinal movement of the shaft.

In another aspect, there is provided a device for self-collection of a biological sample from the vaginal or anal canal during insertion therein, the device comprising:

a rotatable handle;
a body portion connected to the handle;
an insertion portion connected to the body portion at an end thereof opposite the handle, the insertion portion having a longitudinal axis and a tip end having an opening therein, wherein the insertion portion is connected at an angle relative to the body piece, and wherein the angle of connection acts as an impediment to the over-insertion of the device into the orifice;
a flexible shaft housed within said device and extending from the handle to approximately the end of the insertion portion when the shaft is in a retracted position, the shaft comprising a collection end at a distal portion thereof; wherein the shaft is operably connected to an extension mechanism that is activated by rotation of the handle to extend said shaft from the retracted position to an extended position wherein the collection end extends through the opening in the insertion portion; and
wherein the angle of the body portion relative to the longitudinal axis of the insertion piece and the configuration of the insertion piece together position said body portion and handle such that the device is usable for self-sampling while in a seated position when the insertion portion is inserted into the orifice.

In another aspect, there is provided a device for collection of a biological sample during insertion into a human orifice, the device comprising:

a rotatable shaft, wherein the shaft comprises a swab at a distal portion thereof having a plurality of pinwheeling fins each of which has a leading edge oriented to collect the biological sample when the shaft is rotated in a pre-selected direction.

In another aspect, there is provided a kit for collection of a biological specimen comprising:

a container for storing the contents of the kit during the transportation thereof, said container having an upper portion attached to a lower portion, which together define an interior space; and a device for collection of a biological sample, such as that described in any one of claims 1 to 23; and an instructional insert providing information on the kit and its use; and a means of providing user information that uniquely identifies the user; and a tray attached to the lower portion of the container, said tray having a recess for securely holding the device, the instructional insert, and the means of providing user information; the tray configured so that upon opening the upper portion of the container.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 5a is an elevation view of the insertion piece of a specimen collection device.

FIG. 5b is a profile view of the insertion piece of a specimen collection device.

FIG. 5c is a cross-section of the insertion piece of a specimen collection device.

FIG. 6a is a perspective view of the body piece of a specimen collection device.

FIG. 6b is an elevation view of the body piece of a specimen collection device.

FIG. 6c is the left side of a two-piece assembly of the body piece of a specimen collection device.

FIG. 6d is the right side of a two-piece assembly of the body piece of a specimen collection device.

FIG. 6e is an illustration of a possible configuration of a threading mechanism in the body piece of a specimen collection device.

FIG. 7a is an elevation view of the handle of a specimen collection device.

FIG. 7b is a profile view of the handle of a specimen collection device.

FIG. 7c is a cross-section of the handle of a specimen collection device.

FIG. 7d is an illustration of a possible configuration of depressions or grips on the handle of a specimen collection device.

FIG. 7e is a top view the handle of a specimen collection device indicating a possible transverse shape of the handle's channel.

FIG. 8a is an elevation view of the shaft of a specimen collection device.

FIG. 8b is a profile view of the shaft of a specimen collection device.

FIG. 8c is a section view of the shaft of a specimen collection device.

FIG. 8d is a perspective view of the shaft of a specimen collection device indicating differences in cross section along its length.

FIG. 8e is a view of the shaft of a specimen collection device when it is in a curved state.

FIG. 11a illustrates potential alternative configurations of the swab tip of the shaft.

FIG. 11b is a perspective view of the swab tip of the shaft.

FIG. 11c is a cross-section view of the swab tip of the shaft.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the terms "transport" and "deliver" refer to the physical transportation of a sample, sampling device, sampling kit, or any other component of a medical device or component associated with a medical device, from one physical location to another physical location. The physical locations may be geographically separated, such as a laboratory and a patient's home. Alternatively, the physical locations may nearby, proximal, or at a common geographical location, such as a physician's office and a physician office laboratory operating at a common premises, or at nearby premises. In another example, the physical locations may be a core laboratory and an associated hospital or nearby hospital and or a location within a nearby or adjacent hospital network. Transportation may include, but is not limited to, any one of mailing, shipping, delivering, hand delivering, and automated delivery systems such as pneumatic tube delivery systems.

Figure 1:
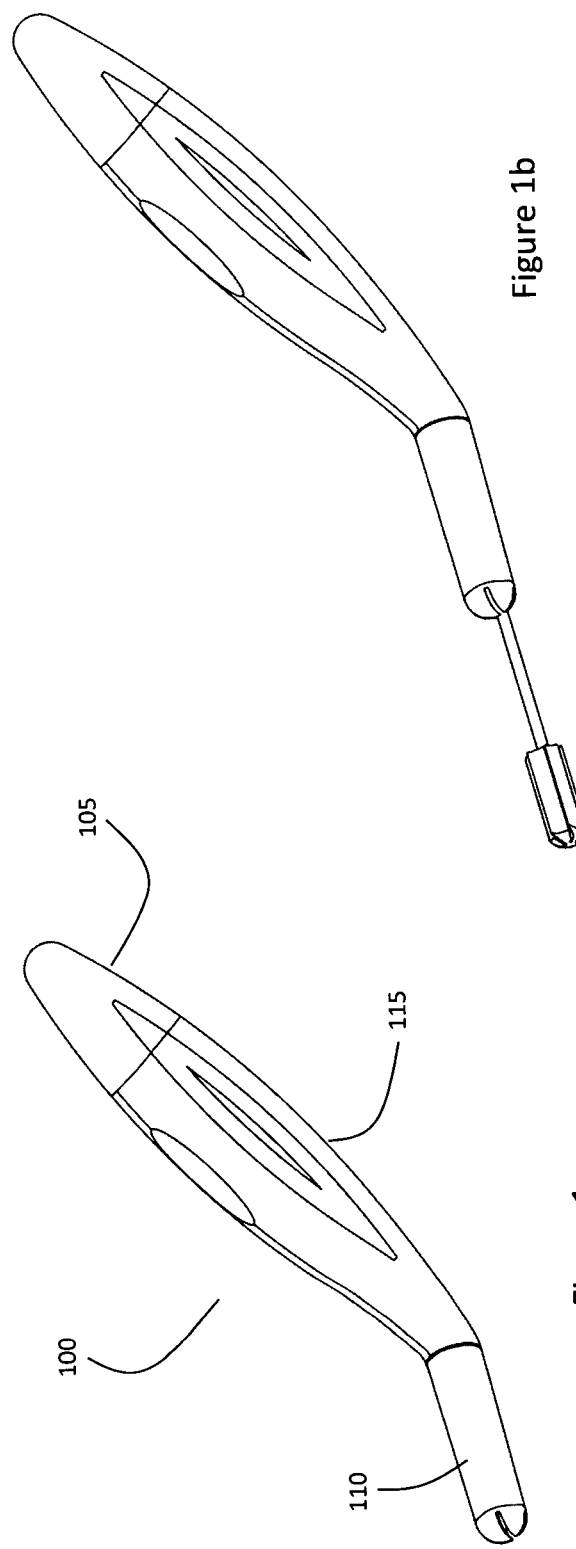
FIG. 1a is a perspective view of a specimen collection device in a retracted position.
FIG. 1b is a perspective view of a specimen collection device in an extended position.

FIGS. 1a and 1b illustrate an example specimen collection device according to an embodiment of the present disclosure. Sample collection device 100 has a rotatable handle 105, an insertion piece or tube 110, and a body piece 115 connecting handle 105 and insertion piece 110 (FIG. 1a).

Figure 2:
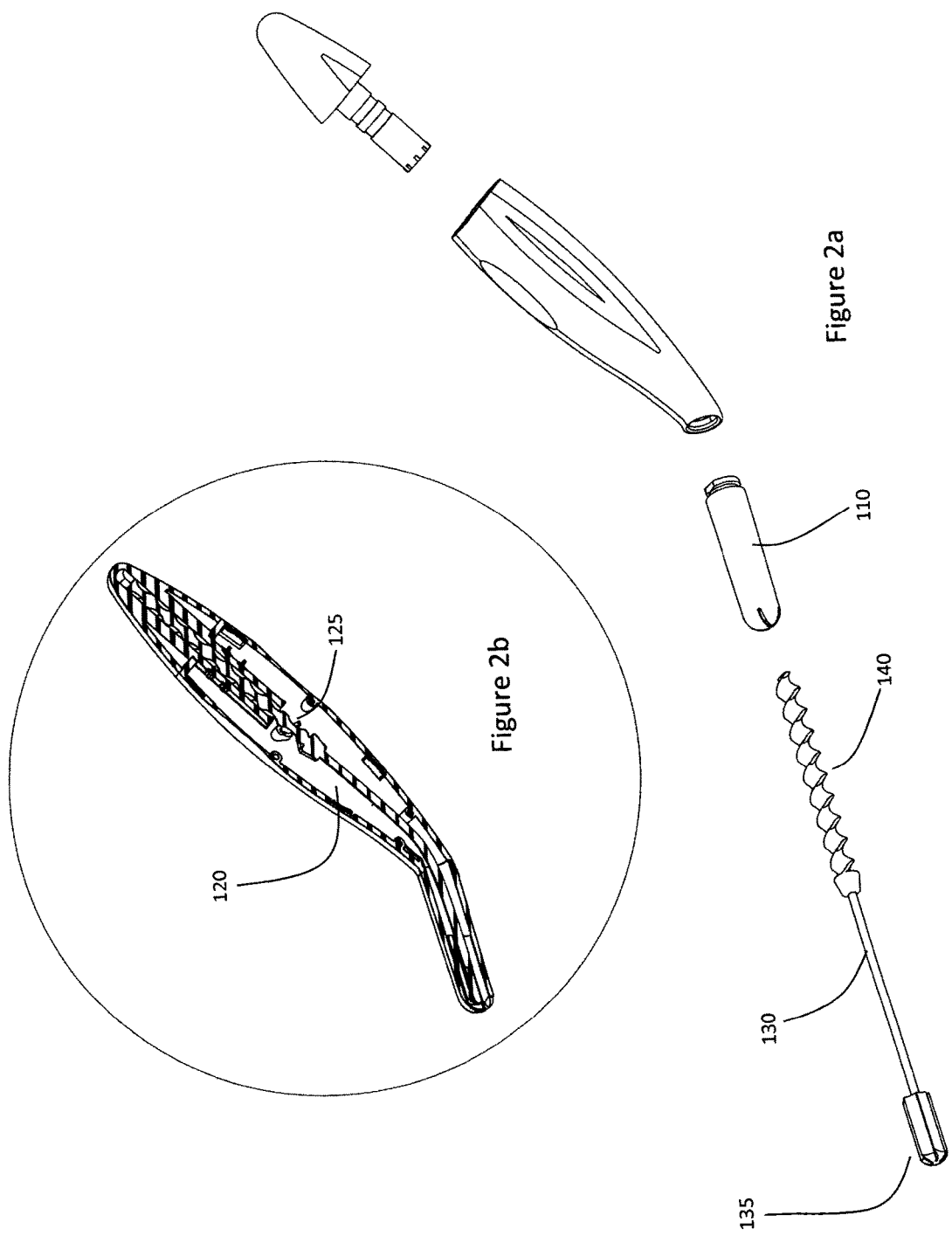
FIG. 2a is an exploded view of the components of a specimen collection device.
FIG. 2b is a sectional perspective of a specimen collection device in a retracted position.

Referring now to FIGS. 2a and 2b, handle 105, body piece 115 and insertion piece 110 together define an interior region, and within the interior region 120 of body piece 115 is a threading mechanism 125. The interior region also houses shaft 130, which is configured to engage threading mechanism 125 and traverse the interior region of the device, extending away from handle 105 and out of insertion piece 110 when shaft 130 is rotated, as shown in FIG. 1b).

In the example embodiment shown in FIGS. 2a and 2b, threading mechanism 125 is shown as a rack that engages with a worm or helical threaded profile 140 on shaft 130. It is to be understood, however, that the illustrated embodiment is but one example of cooperative mechanisms that may be employed to facilitate the extension of shaft 130 under the rotational motion of handle 130. For example, shaft 130 may be extended from the interior region of handle 115 according to a ratcheting mechanism, as described below.

Device 100 may be configured such that in some sampling applications, a sample may be collected during the simultaneous rotation and extension of the collection (i.e. distal) end 135 of shaft 130 when a user turns handle 105 of the device. FIGS. 2a and 2b show the relationship between handle 105, body piece 115, the insertion piece 110, and the shaft 130.

Figure 3:
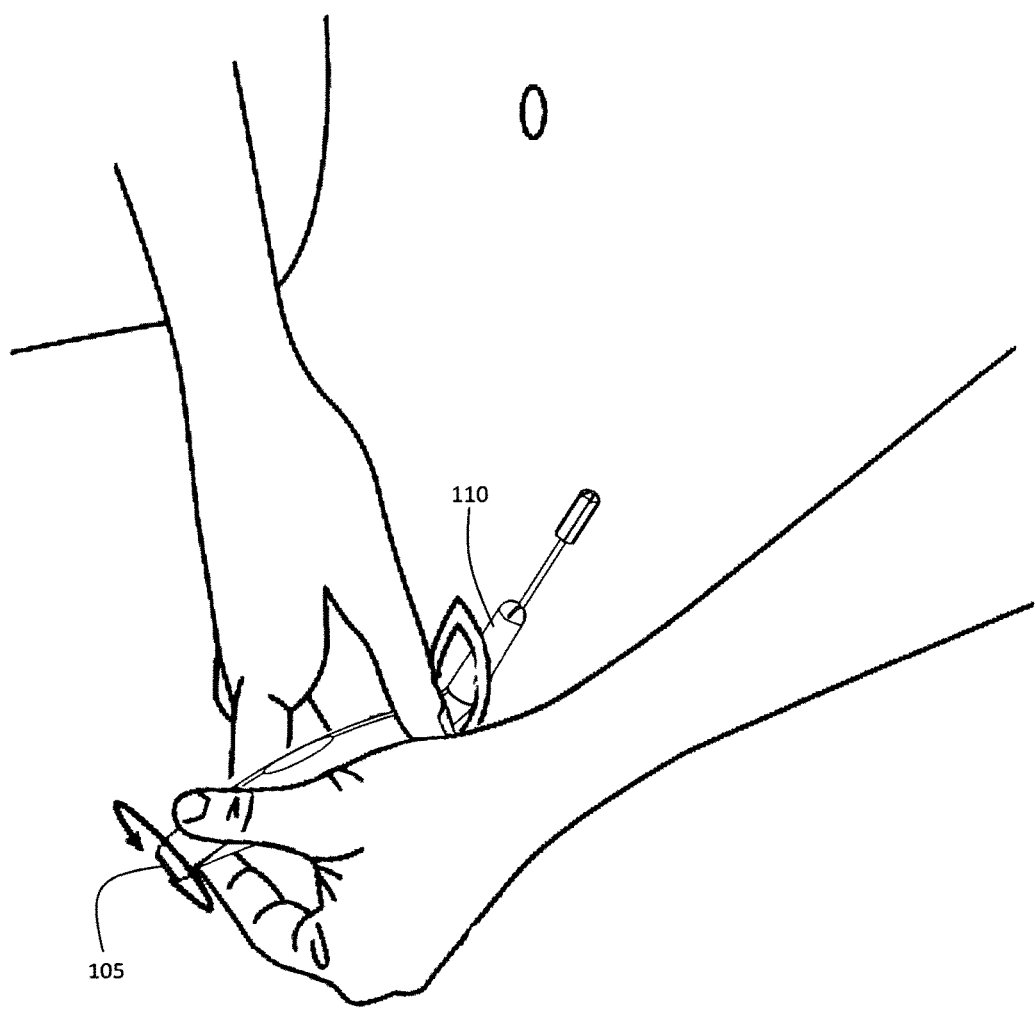
FIG. 3 is an illustration of a user utilising a specimen collection device to collect a vaginal sample.

To initiate sampling, insertion end 110 of the device may be inserted by the user into the vaginal canal, or another orifice such as the anal canal, as shown in FIG. 3. In one embodiment, the connection between body piece 115 and insertion piece 110 is such that there is a small outer channel or reveal between the two pieces on an external portion of the device, in order to indicate the correct distance to which the device is ideally inserted. Alternatively, a visual marking may be provided at the junction of body piece 115 and insertion piece 110. The channel or marking may alternatively be provided on a portion of insertion piece 110 near to, or proximal to, the connection point between the two pieces.

In order to collect a specimen, according to one embodiment, the user may rotate handle 105, which causes the rotation and extension of the enclosed shaft, from a retracted to an extended position, out of and away from, insertion piece 110. In another embodiment, one or more additional pieces, separate from handle 105, may be used to initiate rotation and extension of shaft 130.

Figure 4B:
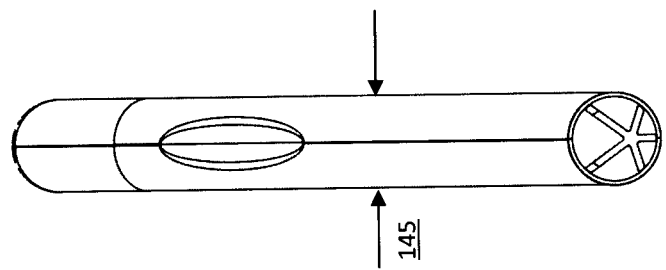
FIG. 4b is a profile view of a specimen collection device.
Figure 4A:
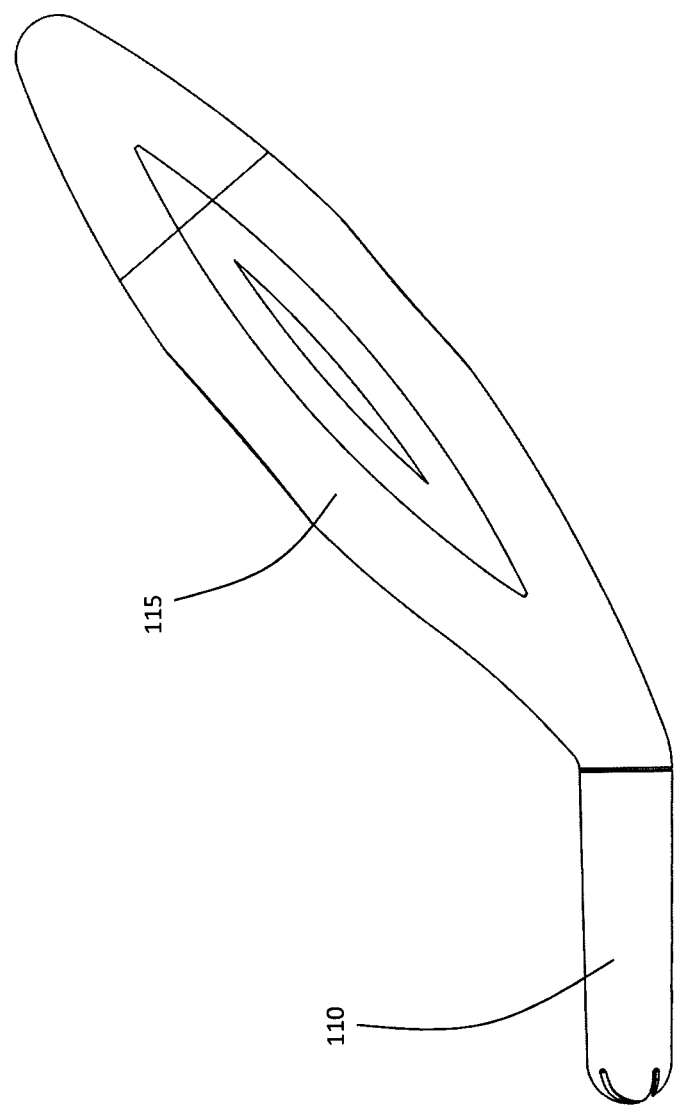
FIG. 4a is an elevation view of a specimen collection device.

According to one embodiment, one or more portions of the sample device may be curved, bent, or otherwise shaped in order to facilitate device use, and/or to accommodate a natural biological geometry or curvature. FIG. 4a illustrates one such example embodiment, where insertion piece 110 is angled relative to body piece 115. This shape, where the longitudinal piece 105 is angled relative to the longitudinal axis of body piece 115, makes it easier for a user to hold and to rotate the handle while the insertion end is inserted into the vaginal canal, or another body orifice such as the anal canal. This ease of use is illustrated in FIG. 3, where body piece 115 is shown oriented in an approximately horizontal orientation during sampling, while insertion piece 110 is angled upwards within the vaginal canal, thereby accommodating sampling in an ergonomic fashion. For example, this orientation enables a user to remain seated during sampling, without having handle 105 angled downwards and potentially contacting the seating surface. In some embodiments, the angle between the insertion portion and the body piece is at least approximately 15 degrees.

The angle or curvature design also assists to prevent injury, for example, by acting as an impediment to prevent a user inserting the device too far into an orifice (i.e. over-inserting the device). In another embodiment, the device may be gradually curved, as opposed to angled at a specific location. In other embodiments, the relationship between insertion piece 110 and handle 105, or between insertion piece 110 and any other piece or component used to rotate shaft 130, may be an angle, without the overall shape of the device itself being angled or curved. In profile, the left and right sides of the device may be planar or approximately planar, as shown in FIG. 4b, such that the device can be laid flat on either side. According to one embodiment, the device may be narrow in profile, such that the distance between planar sides 145 is such that, along with packaging, the device may be shipped by standard mail. For example, in one example implementation, the device is less than 20 mm in thickness.

Referring now to FIGS. 5a-c, insertion piece 110 comprises a connection end 150 opposite a tip end 155. Connection end 150 is configured to connect to body piece 115 of the device, and includes an internal open region 160 to allow movement of the shaft 130 within body piece 115 and the insertion piece 110.

In one embodiment, tip end 155 of insertion piece 110 may be rounded, as shown in FIGS. 5a-c and made of a smooth material, such that it causes minimum friction or discomfort upon insertion into an orifice. Tip end 155 is configured to allow the emergence, extension, and optional retraction of shaft 130. For example, on one embodiment, tip end 155 may include a deformable opening formed by multiple cuts such that two or more portions of tip end 155 are deformable upon passage of shaft 130 through tip end 155. In one such embodiment, tip end 155 may include a star-shaped opening 165, as shown in FIG. 5b. In another embodiment, the opening of tip end 155 may be such that collection end 135 of the shaft 130 (shown, for example, in FIG. 2a) is not enclosed within insertion piece 110, but nevertheless abuts or is proximal to the opening of tip end 155 while shaft 130 is in the retracted position. Other configurations, which similarly minimize discomfort upon insertion and allow the passage of the device shaft during extension of the device through an opening in the tip end, may be employed without departing from the scope of the present disclosure.

In one particular embodiment, star-shaped opening 165 in tip end 155 may be off the center of tip end 155 of insertion piece 110, as shown in FIG. 5b. In other words, the opening in tip end 155 may be positioned off-axis, for example, such that the opening is provided at a location that is not collinear with the longitudinal axis of insertion piece 155. This off-center (or off-axis) opening causes flexible shaft 130 to emerge from the opening at an angle or bias relative to the longitudinal axis of insertion piece 110 during extension. This angled extension causes collection end 135 of shaft 130 to rotate in a wider circle (relative to extension that is collinear with the longitudinal axis of insertion piece 110), and thus maintain more sustained or forceful contact with the vaginal walls. This nutation during extension may be effective in increasing the efficiency of sample collection, especially in applications in which it is beneficial to sample tissue adhered to or forming an outer layer of a lumen wall. This configuration of the opening of tip end 155 and shaft 135, due to potential energy stored in the curve of the shaft 135 towards its base, may enable the shaft to oscillate as it extends.

In applications involving the collection of a biological sample within the vaginal canal, the insertion piece 110 may be of a length between approximately 25 mm-45 mm, and the shaft 130, when extended, may be of a length between approximately 60 mm and 100 mm from the base of the insertion piece to the collection end 135. It will be understood that these dimensions are provided as one illustrative example for the collection of a biological sample from the vaginal canal, and that other dimensions may be more suitable in other applications or uses.

Body piece 115 of the device is shown in more detail in FIGS. 6a-6e. It is configured to accept or connect to handle piece 105 of the device at proximal end 180 and to insertion piece 110 at distal end 175. In one embodiment, body piece 115 may be configured to connect to handle piece 105 and insertion piece 110 in a curve, as described above, and this curve may be ergonomically designed to fit the hand of a user, or to otherwise aid in the use or handling of the device. The exterior surface of body piece 115 may be outfitted with grips 171, as shown in FIG. 6a, or using another non-slipping or textured surface profile or composition, to aid the user with the proper handling and alignment of the device while in use. As described above, body piece 115 encloses an interior region 120 and has interior walls to which the threading mechanism 125 (e.g. rack) is attached, or integrally formed. Body piece may be constructed of one or more (e.g. two) separate pieces (such as in FIGS. 6c and 6d). For example, two separate pieces facilitate easy access to the interior or threading mechanism 125 of body piece 115, or to shaft 130. The two pieces can be attached by means of snaps, pins, adhesives, sonic welding, or other suitable means known to those skilled in the art. The body piece may be configured so that its volume is larger at regions where required by the inner mechanical workings which it encloses, which may take the form of localized convexities 185.

In one example embodiment of the device, shaft 130 has a helical segment 140 (as shown, for example, in FIG. 2a) which may rest within threading mechanism 125 when shaft 130 is either in the retracted or extended position. In another embodiment, shaft 130 may be pushed into or out of a position in which it can engage threading mechanism 125 during the operation of the device.

According to the example embodiment shown in FIGS. 6a-6e, upon rotation of shaft 130, helical segment 140 interacts with threading mechanism 125 such that the rotation of shaft 130 is translated into lateral movement and shaft 130 is pulled through the mechanism along the shaft's length as it rotates.

In one embodiment, threading mechanism 125 may be formed by an interlocking double x shape (as shown in FIG. 6e), fitting the contour of the helical end of the shaft. In the example mechanism shown in the Figure, a pair of hook members 127 are provided extending from the inner surface of the body member, where the hook members 127 are positioned and oriented in a double-x configuration that is suitable for engaging the helical thread on the shaft. In another embodiment, a single interlocking x in a similar configuration may be used.

In yet another embodiment, the threading mechanism may make up the negative space of the helical portion of the shaft within a fixed volume of appropriate size. Other shapes and configurations of the threading mechanism that accomplish the same or a similar function, namely to allow the rotation of the shaft and propel it along its length using its own rotational force, may be employed.

In one embodiment, the threading mechanism and device shaft are configured so that the clockwise rotation of the shaft causes the extension of the device and the counter-clockwise rotation of the shaft causes its retraction. A mirrored configuration in which the converse is true (i.e. clockwise rotation causes retraction, counter-clockwise causes extension) is also possible. In another embodiment, a stop may be added to either the shaft 130 or the threading mechanism 125, or both, or the length of the shaft 130 or the handle sleeve (or channel) 210 adjusted, such that the device is capable of extension from an initial position, but not of retraction from an extended position. Additionally, a stop may be placed on the body piece 115, or the threading mechanism 125, or the shaft 130, or a combination of the above, to prevent the extension from going too far and the shaft 130 from disengaging either the threading mechanism 125 or the sleeve.

In yet another embodiment, the shaft or threading mechanism or both may be outfitted with a ratcheting system so that the device is capable of extension from an initial position, but not of retraction from an extended position; alternately, such a configuration may be calibrated so that retracting is more difficult than extending (or vice versa), or so that the device produces haptic feedback or sound, such as a clicking sound, on each rotation or part thereof.

Handle 105 of the device is shown in more detail in FIGS. 7a-e. In one example implementation, handle 105 has a grip end 200 and a connection end 205, the latter of which has an opening to an interior sleeve (or channel) 210, as shown in FIG. 7c. In the example embodiment shown, grip end 200 of handle 105 is of a shape continuous with the exterior of the body piece, but in other embodiments, the grip end 200 may be of another shape suitable for holding or manipulation by the user. In one embodiment, the exterior surface of handle 105 may contain depressions that facilitate a user holding or manipulating the handle. In yet another embodiment, depressions may be placed on diametrically opposite sides of the handle, and contoured to a thumb on one side and a finger on the other, such that it encourages the user to grip the handle in a way that anticipates its correct rotation, as shown in FIG. 7d.

Connection end 205 of handle may be smaller in dimension than the exterior of the body piece of the device, such that it can be enclosed within the body piece. In one embodiment, connection end 205 may be cylindrical, with cylindrical bands 215 forming an interlocking connection mechanism with the body piece, which, when assembled, does not allow it to be withdrawn from the body piece, but nevertheless allows it to rotate freely within the housing on the interior of the body piece.

In another embodiment, the bands may be notched, for example, in a serriform manner, so that the handle can be pushed into place but not withdrawn. Other shapes and methods of interconnection between the handle and the body piece that allow the handle to interlock securely with the body piece while still rotating freely within it may be envisioned by one skilled in the art.

As shown in FIGS. 7a-7e, handle 105 defines sleeve 210 which is open at connection end 205 of handle 105, and in one embodiment may be closed at grip end 200, or may, in other embodiments, be open on both ends of handle 105.

Sleeve 210 is configured to receive the insertion of shaft 130 of the device. In one embodiment, the sleeve 210 has a cross-section that is planar on two facing sides and connected by two arcs on the opposite sides, as shown in FIG. 7e, having the appearance of a circle with planar cuts on either side. Such a cross-sectional shape accommodates the maximum cross-sectional dimension of the helical end of the shaft at all points along its length (i.e. the cross-sectional shape is complementary to that of the helical portion of the shaft). This configuration allows the turning of the handle, and thus the rotation of the sleeve, which imparts a rotational force on the shaft so that the shaft and handle rotate concomitantly, causing the shaft to engage threading mechanism, thereby leading to the translational movement of the shaft along the interior of the device. Other configurations which allow this relationship—such that shaft 130 rotates and engage the threading mechanism without impeding its translational movement along the interior—may be employed without departing from the scope of the present disclosure.

Referring now to the example embodiment shown in FIGS. 8a and 8b, shaft 130 of the device includes helical segment 140 and collection end 135, which may include rod 220 and swab 225. In another embodiment, the helical segment 140 of the shaft may be a discrete piece from the collection end, and these two may be attached, whether mechanically, adhesively, or by some other process. In yet another embodiment, the helical portion of the shaft may run along the whole length of shaft 130 between its base and swab 225.

In one embodiment, helical segment 140 of the shaft (see FIG. 8d) may be a helix that has a non-circular cross section, such as an oval-like cross section, that is rotated along its length. In this embodiment, two sides of the helix may be planar, so that the helix may appear as a standard helix with two parallel sides partially sheared off, in which case the spiralling cross-section of the helix would alternate between an oval and an oval truncated in its longer dimension (i.e. the overall cross-sectional dimension of the shaft is not a circle but a truncated circle with two parallel sides) as shown in FIG. 8a.

Such a shape allows for shaft 130 to be subject to a rotation or spiralling motion, when engaged by the threading mechanism of the device, along the entire length of its helical portion, while at the same time accepting a rotational force from an object (in the present embodiment, handle 105) to which it is not attached or affixed, and thus to be capable of rotating and being translated along both the threading mechanism and the object imparting the force, while these last two undergo no translation. Put otherwise, the shape of helical segment 140 of shaft 130 may be such that, along its entire length, the rotation of the handle will cause the shaft to rotate (i.e. the handle will not spin around it), to engage the threading mechanism, and to be pulled equally along and through both the threading mechanism and the sleeve of the handle. This allows the simultaneous rotation and extension of shaft 130 with a minimum number of parts and without the need of a lateral (pushing) force from a user's hand or other mechanism.

As shown in FIG. 8c, which provides a cross-sectional illustration of the shaft and swab, the swab may contain a channel 136 into which the shaft is inserted, such that the swab is separable from the shaft by pulling the swab tip away from the shaft.

The rod 220 of the collection end of shaft 130 may connect the helical segment 140 of the shaft to the swab tip 225. In one embodiment, it may be made from plastic or such other material with sufficient elasticity to the follow the curve between handle and insertion piece without permanent deformation (FIG. 8e).

Figure 9A:
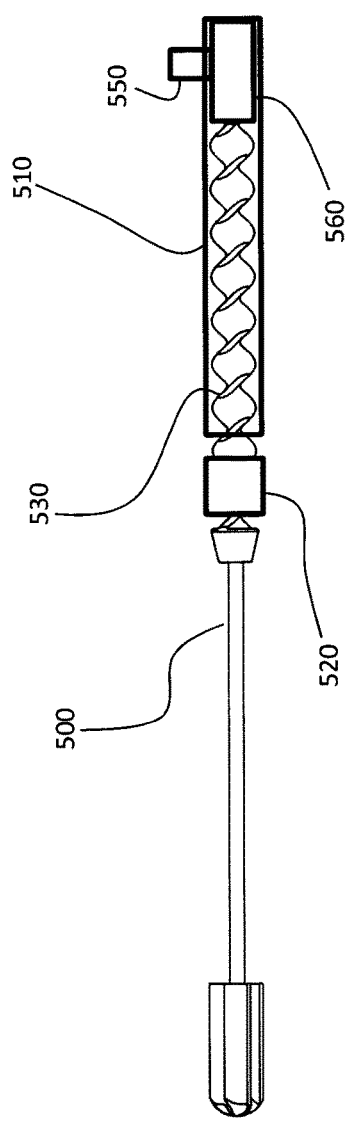
FIG. 9a is a schematic illustration of one embodiment of the relationship between the shaft, the sleeve, and a threading mechanism, where the shaft is in a retracted position.
Figure 9B:
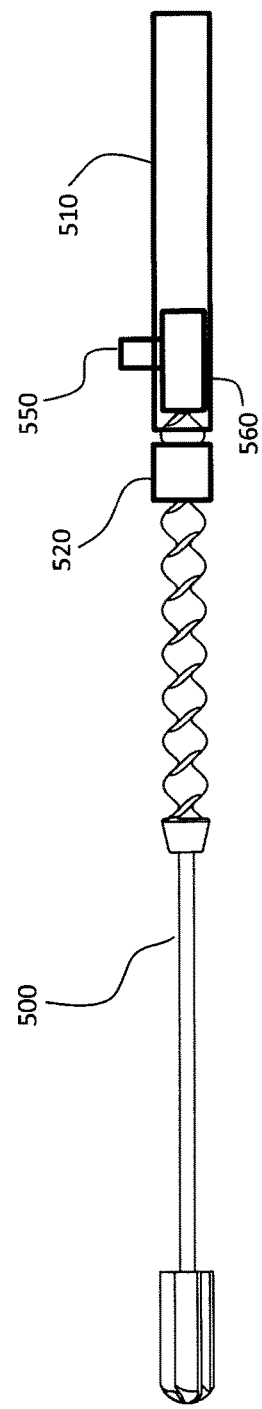
FIG. 9b is a schematic illustration of one embodiment of the relationship between the shaft, the sleeve, and a threading mechanism, where the shaft is in an extended position.

It will be understood that the embodiment shown in FIGS. 6a-e, 7a-e, and 8a-e represent one illustrative example of a device configuration in which the rotation of the handle produces rotating extension of the shaft due to the engagement of the threaded portion of the shaft with the threading mechanism and the contact between the rotating sleeve and the shaft. Another example embodiment is shown in FIGS. 9a and 9b, which schematically illustrates the relationship between the shaft 500, the sleeve 510, and a threading mechanism 520. The body piece, which supports threading mechanism 520 (i.e. threading mechanism 520 may be attached to, or integrally formed within, the body piece), is not shown. Similarly, the handle, which supports sleeve 510, such that sleeve 510 rotates concomitantly with the handle, is also not shown. In the present embodiment, shaft 500 includes a threaded portion 530 having a circular thread that is engaged by threading mechanism 520. Threading mechanism 520 may be a pair of hook members configured to engage with the circular thread on threaded portion 530 of shaft 500, in a manner similar to that described for the preceding embodiment. In another example, threading mechanism 520 may be a structure having a cylindrical bore with an inner thread configured to engage with the external circular thread on threaded portion 530 of shaft 500. Sleeve 510 includes a longitudinal slot or aperture (residing in the plane of the page in FIGS. 9a and 9b) that receives a protrusion 550, which is connected to a proximal portion 560 of shaft 500, and allows longitudinal movement of shaft 500.

Upon rotation of the handle, the concomitant rotation of sleeve 510 applies a torque to shaft 500 due to contact between sleeve 510 and protrusion 550. In other words, sleeve 510 contacts shaft 500 through protrusion 550. The torque rotates shaft 500 concomitantly with the handle, and threading mechanism 520 produces longitudinal motion (extension or withdrawal) of shaft 500 during the rotation due to the engagement of threaded portion 530 with threading mechanism 520. The structure therefore produces rotation and longitudinal translation of shaft 500 under rotation of the handle. It will be understood that proximal portion 560 of shaft 500 may be a proximal portion of threaded portion 530, and need not be an unthreaded portion as shown in the Figure.

In another embodiment, the diameter of the rod (or shaft generally) may be smaller at a specific breakpoint (not shown), thus allowing the shaft to be broken in a controlled manner when a shear force is applied, such that the swab tip, and where desired other parts of the shaft, can be broken off and separated from the shaft and/or device; in such case, the material of the shaft may be sufficiently stiff or brittle to allow this without breaking unintentionally in normal operation of the device. In one embodiment, the location of the breakpoint may be indicated by an arrow, coloured strip, or other indicator.

Figure 10:
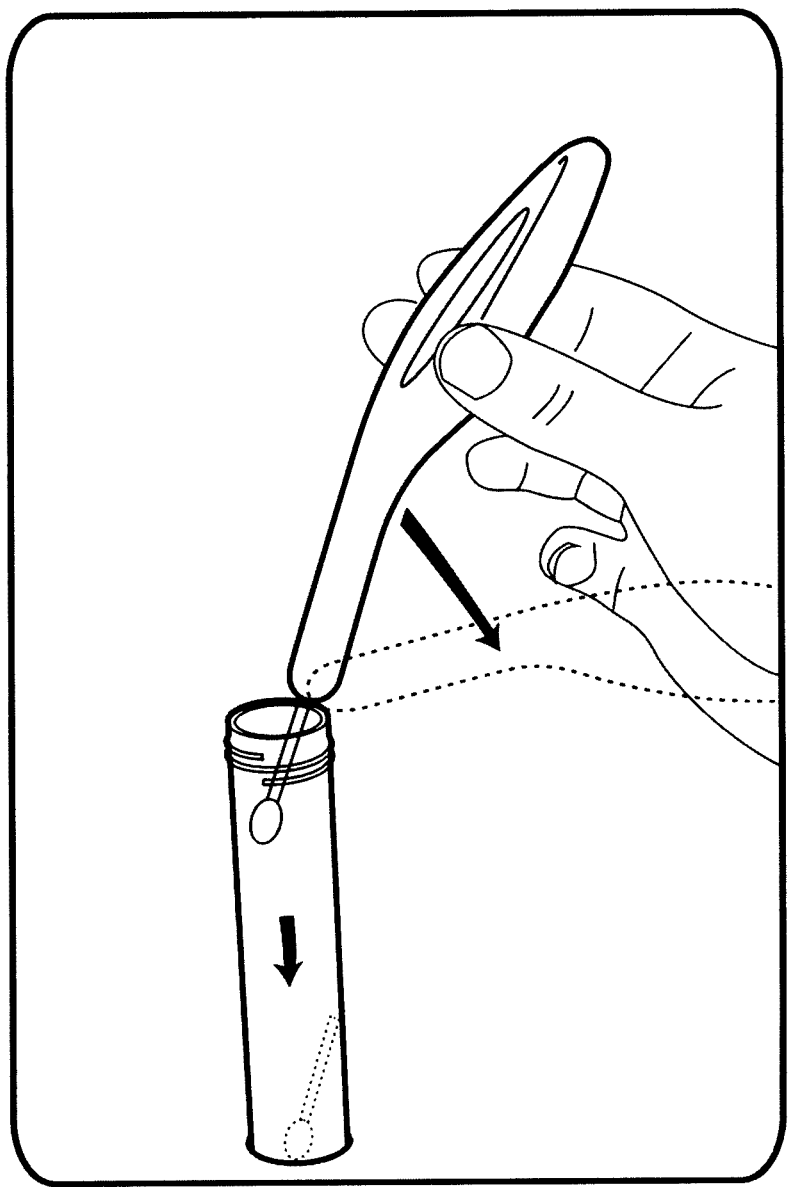
FIG. 10 is an illustration of a user breaking off the swab tip of the shaft using the rest of the device to leverage it against the tip opening of the insertion piece.

In one embodiment, the breakpoint on the shaft of the device may be positioned such that, when the device is in an extended position, it abuts or is otherwise proximal to the opening of the tip end of the insertion piece. This allows the whole device to be used as leverage to facilitate the breaking of the shaft at the breakpoint, as shown in FIG. 10. This also precludes breakage during extension of the device, which may otherwise occur if the breakpoint is located at an intermediate location.

The swab tip 225 may be made from material (such as bristles 235, or an absorbent material, for instance, sponge or foam) and in a configuration, as illustrated (FIG. 11*a*) or otherwise, suitable for the collection of biological specimens.

In one embodiment, the swab tip is composed of radiating or pinwheeling fins 230 such that when the shaft and swab tip are rotated, the extremity of the fin forms a leading edge 240, which will collect from or scrape the desired sampling area (FIG. 11*b*). Further, the interior of the space between fins may have channels 245 (as seen in FIG. 11*c*) running along the connection between fins such that collected cellular material, or fluid (vaginal or otherwise), or other biological material may come to rest and be stored in them; in addition, the channels may be appropriately sized or otherwise configured such that fluid biological material may rest and be stored in them by capillary action.

The swab may be configured to change colour in order to indicate to the user that they have (successfully) collected a sample. In one embodiment, this may be accomplished by the insertion of dye under the surface of the swab tip, such that, when the swab tip is sufficiently moistened, by vaginal fluid or other biological material, the dye spreads to the surface of the swab tip or is otherwise activated, causing the swab to change colour. In another embodiment, the swab tip may be coated in a pH sensitive solution, reagent or material, such that when it is coated in biological material within the desired pH range, it is activated or changes colour; in one specific instance of this, the pH of the covering substance may be calibrated, as narrowly or widely as desired, to the pH of a reasonably healthy vaginal environment.

Apart from the swab tip, the device may otherwise indicate the successful collection of a sample. In one embodiment, the extension of the shaft to a completely extended position may physically puncture a dye pack, after which the dye would become visible to the user, through, for instance, a 'window' or transparent area (not shown) in the exterior surface of the device. In another embodiment, a part of the shaft may be differentially coloured, such that a colour indicating success will only become visible, through a window in the exterior surface of the device, or at the opening of the tip end of the insertion piece, when the device is fully extended.

Figure 12A:
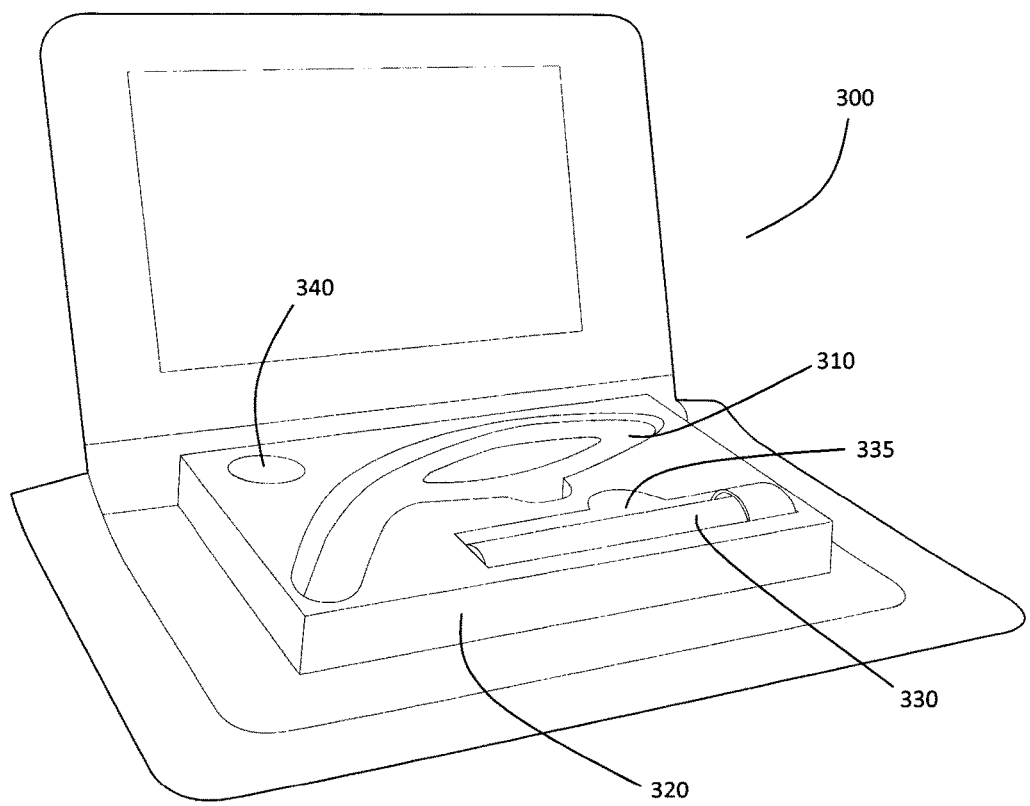
FIG. 12a is a perspective view of a sample collection kit.

FIG. 12*a* illustrates an example kit 300 for the collection of biological specimens. The kit may be employed for collecting, storing, identifying and/or transporting biological samples, such as biological tissues, cells, and/or fluids. The example kit includes a device for the collection of specimens according to any of the aforementioned embodiments, and a package that is suitable to be transported. The package includes recesses 310 for supporting the device, and may be employed to support one or more components of the kit during the sampling process, as further described below. The package is configured for storing a sample, transporting a sample, and recording patient information associated with the sample (for example, for uniquely identifying and/or tracking the sample). The package also includes an instruction insert providing information on the kit and its use.

In one example implementation, the kit may be transported to a patient's home, where the patient can use the device for the self-collection of a biological sample, such as, but not limited to, a vaginal fluid sample. The patient may store the sample in a manner suitable for safe transportation, and transport the sample and relevant patient information by mail to a lab. In some embodiments, only a portion of the device is transported in the package after having performed a sampling operation.

Alternatively, the kit may be given directly to the patient by a healthcare provider or other individual. In yet another example, the specimen collected may be delivered directly, or otherwise, to the laboratory.

Further, the kit could be adapted to provide, immediate, point-of care diagnosis for HPV, or other markers, including, but not limited to, chlamydia, gonorrhea, trichomoniasis, herpes, syphilis, bacterial vaginosis, or colon cancer. For example, in some embodiments, the kit may include one or more rapid test devices for conducting an assay based on the collected sample. The rapid test device may be a lateral flow based test device.

Figure 12B:
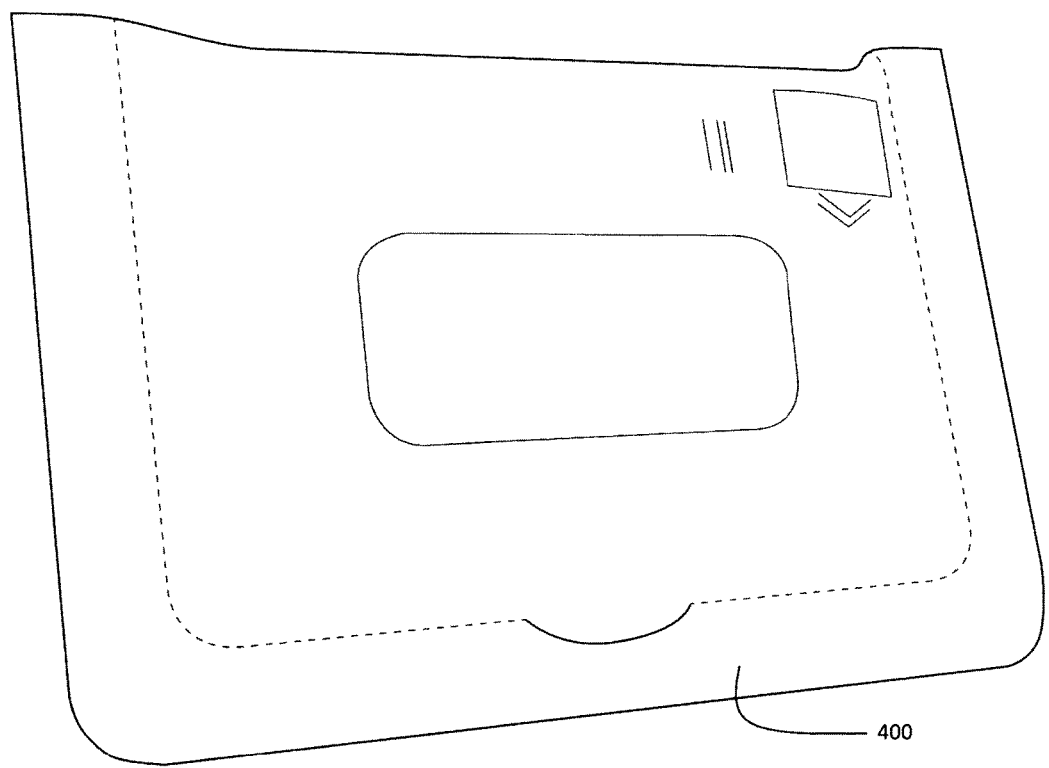
FIG. 12b is a view of the mailing package of a sample collection kit prior to be opened.

A mailing package of the specimen collection kit is shown in FIG. 12*b*. The package defines an exterior 400 of a dimension and composition that may be transported, e.g. by standard (letter) post, and may enclose the specimen collection device, instructions for use, a means of tracking patient information and results, a means of storing and preserving collected specimens, and a means of returning samples by mail. The package may be shipped directly to the home of a user or patient, or distributed via another means, and used by the patient to collect a specimen, after which it may be used to ship, or return by other means, the specimen a laboratory or other suitable location; in cases where a diagnosis or other test can be provided on site (e.g. point-of-care), a method may be provided for users to share those results with, for instance, a health care practitioner.

The exterior of the mailing package may be constructed of a paper, or card, or foil, or plastic, or other material suitable to its form and function (e.g. sufficiently strong to avoid being ripped or damaged during shipping). In one embodiment, the exterior of the mailing package may be constructed of a single sheet of material that is folded over and sealed, by heat, adhesive, mechanical, or other means, and may be perforated along or near its edge to allow it to be opened in a controlled manner by the user without special tools.

Figure 12C:
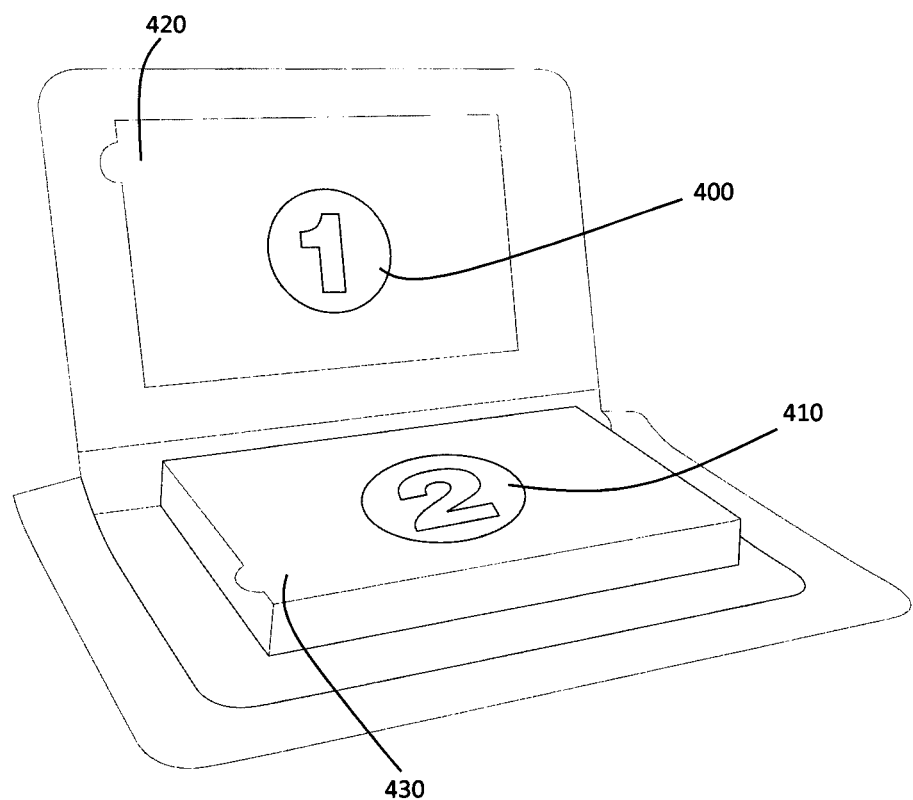
FIG. 12c is a view of a sample collection kit with removable numbered sheets.

A potential configuration of the interior of the mailing package is shown in FIG. 12*c*. In one embodiment, the interior may have numbers, letters, or other markings 400, 410, displayed prominently or otherwise (via direct printing, stickers, tabs, etc.) that indicate the correct order of use of the components in the package. In one specific instance of this embodiment, stickers, tabs, or perforated sheets (e.g. a thin, removable expanse) may be marked and configured as labels 420, 430, such that the user may access that part of the package that they should use next by peeling off or removing the marked label (e.g. to perform Step 1 in using the kit, the user would pull off the sticker marked 1 (shown at 400) and use the component of the kit thereunder, followed by the sticker marked 2 (shown at 410), etc . . . ).

In one embodiment of the specimen collection kit, the mailing package may be shipped with a specific identification number or code that uniquely identifies the desired patient or user; this could be taken automatically or otherwise from a registry of desired users, or some other form of patient or user database, or could be generated automatically upon manufacture or assembly of the kits. In another embodiment, the user may be required to input information, either manually or digitally, to uniquely identify the sample as belongs to the user, and to enable its tracking via a database. In yet another embodiment, some combination of the above methods may be used; for instance, the package may be shipped with a unique identifier that identifies and tracks the specimen (e.g. during lab processing), while the patient may be required to enter or keep additional information to link their personal identity to that unique identifier.

Figure 12D:
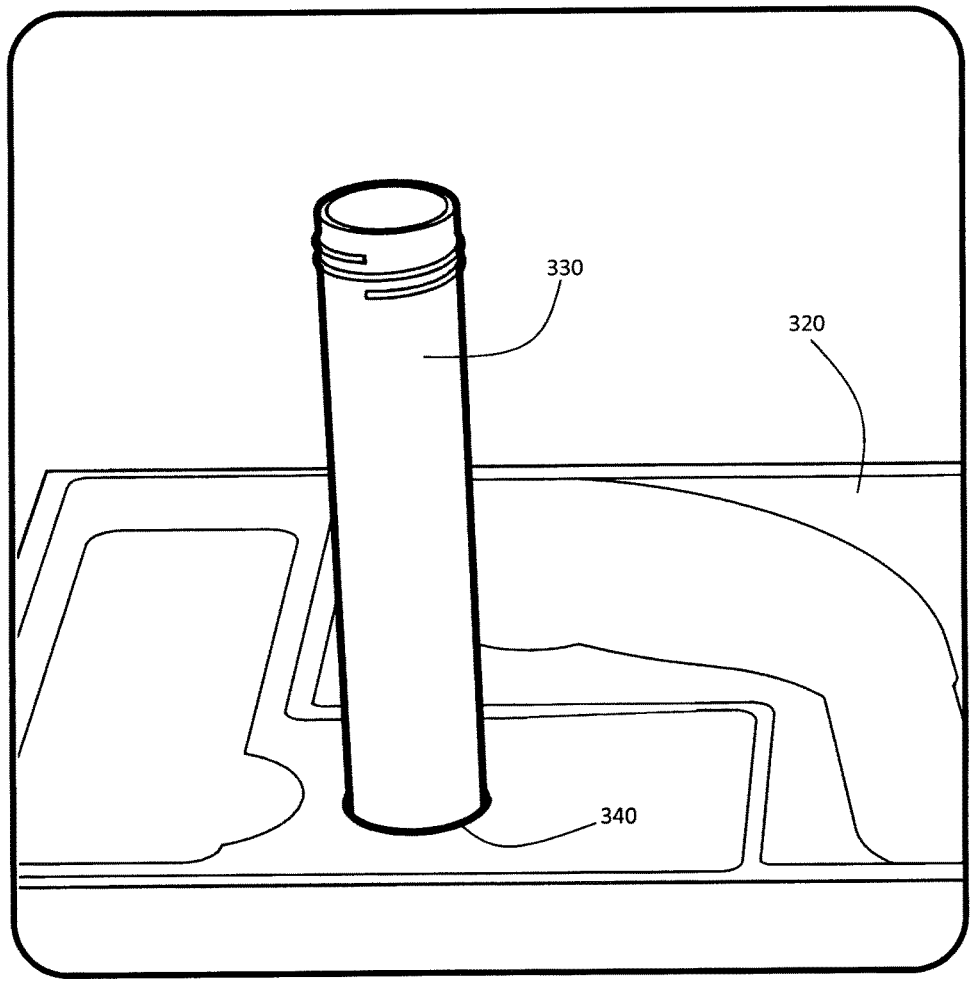
FIG. 12d is a view of the tray of the mailing package with a container of preservation medium held upright in a slot created for that purpose.

Referring to FIGS. 12a and 12d, the kit may also contain a tray 320, that is designed to securely hold the device and the other components of the kit. The tray 320 may be integrally connected or may be of one piece with the exterior of the mailing package. The tray 320 may be made of vacuum-formed plastic or other material that is sufficient to its purpose. In one embodiment, where the kit contains a buffer, alcohol solution, or other means of preserving and storing the specimen once collected, the kit may include a vessel 330 for this preservative, where vessel 330 is stored in recess 335. Apart from this designated place, which is suitable for transportation and shipment of the kit, the tray can also have an indentation 340 that allows vessel 330 of preservative fluid to be placed into it, such that the vessel 330 is held upright by the tray 320 (FIG. 12d). This allows the user to have the vessel 340 of preservative fluid held steady without using their hands to do so.

The mailing package may contain a pre-addressed stamped envelope for the return of a collected specimen, along with any designations and notifications regarding its status as a biological sample. In one embodiment, where a preservative medium is required, the swab tip of the device may be broken off, as described above into the container of preservative medium, and the return envelope may be configured to fit and protect the container of preservative. In another embodiment, a container of preservative may be formatted to fit the entire device, such that the swab tip would not need to be broken off. In another embodiment, the return envelope may be coated or filled with a preservative solution or medium that allows the swab tip or the whole device to be placed in the envelope without an additional container for said preservative. In yet another embodiment, the swab tip or the entire device may be placed in the return envelope without a preservative, and in such case the envelope would be configured to securely protect the collected specimen and minimize sample degradation. Such a preservative may be provided in the form of an internal coating.

It is to be understood that the devices and kits disclosed herein may be employed for the testing of a wide range of diseases and/or analytes, including, but not limited to, anal HPV, Gonorrhea, Chlamydia and Trichomoniasis and Syphilis. This sample collection kits disclosed herein may also be useful in reactive testing (similar to a pregnancy test), which is likely to also be applied to HPV, Chlamydia and other diseases. The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A device for collection of a biological sample during insertion into a human orifice, the device comprising:
    a rotatable handle comprising a sleeve;
    a body piece attached to the handle;
    an insertion piece attached to the body piece opposite the handle and extending therefrom to a tip end having an opening therein; wherein the handle, body piece, and insertion piece together define an interior region;
    a threading mechanism fixed to an inner wall of the body piece at a location beyond a distal end of the sleeve;
    a flexible shaft received within the sleeve, wherein the flexible shaft extends within the body piece and the insertion piece from the sleeve when the shaft is in a retracted position, the shaft having a collection end at a distal portion thereof and a threaded segment configured to engage the threading mechanism beyond the distal end of the sleeve, the shaft being movable from the retracted position wherein the collection end is enclosed within the insertion piece to an extended position wherein the collection end exits the opening in the insertion piece; and
    wherein the sleeve contacts the shaft upon rotation of the handle such that the sleeve and shaft rotate concomitantly, and wherein the threaded segment engages the threading mechanism during rotation of the handle such that the rotation of the shaft is translated into longitudinal movement of the shaft.

2. A device according to claim 1, wherein the orifice is a vaginal orifice.

3. The device according to claim 1, wherein an inner surface of the sleeve a non-circular cross-sectional profile, and wherein the shaft has a complementary cross-section over the portion thereof received within the sleeve.

4. The device according to claim 3 wherein the sleeve non-circular cross-sectional profile is planar on two facing sides that are connected by two arcs on the opposite sides.

5. The device according to claim 1, wherein the handle contains depressions on diametrically opposite sides thereof and contoured to a thumb on one side and a finger on the other.

6. The device according to claim 1, wherein the angle of the body portion relative to a longitudinal axis of the insertion piece positions said body piece and handle such that the device is usable for self-sampling while in a seated position when the insertion piece is inserted into the orifice.

7. The device according to claim 1, wherein the collection end comprises a swab having a plurality of pinwheeling fins, each of which has a leading edge oriented to collect the biological sample when the shaft is rotated in a pre-selected direction.

8. A device for self-collection of a biological sample from the vaginal or anal canal during insertion therein, the device comprising:
    a rotatable handle;
    a body piece connected to the handle;
    an insertion portion connected to the body piece at an end thereof opposite the handle, the insertion portion having a longitudinal axis and a tip end having an opening therein, wherein the insertion portion is connected at an angle relative to the body piece, and wherein the angle of connection acts as an impediment to the over-insertion of the device into the canal;
    a flexible shaft housed within said device and extending from the handle to approximately the end of the insertion portion when the shaft is in a retracted position, the shaft comprising a collection end at a distal portion thereof; wherein the shaft is operably connected to an extension mechanism that is activated by rotation of the handle to extend said shaft from the retracted position to an extended position wherein the collection end extends through the opening in the insertion portion; and wherein the angle of the body piece relative to the longitudinal axis of the insertion piece positions said body piece and handle such that the device is usable for self-sampling while in a seated position when the insertion portion is inserted into the canal.

9. The device according to claim 8, wherein the body piece is curved.

10. The device according to claim 8 wherein the angle between the insertion portion and the body piece is at least approximately 15 degrees.

11. The device according to claim 8, wherein the opening at the tip end of the insertion portion is off centre relative to a longitudinal axis of the insertion portion so as to direct the shaft at an angle relative to the longitudinal axis during extension thereof.

12. The device according to claim 8, wherein the angle of the body piece relative to the insertion portion is generated by a gradual curve.

13. The device according to claim 8, wherein the shaft is curved.

14. The device according to claim 8, wherein the shaft has a breakpoint for separating the collection end from the shaft by a shear force.

15. The device according to claim 14, wherein the breakpoint is proximal to the opening of the tip end of the insertion portion when the device is in the extended position.

16. The device according to claim 8, wherein either the shaft comprises a stop such that the shaft is capable of extension from the retracted position, but not of retraction from the extended position.

17. A device for collection of a biological sample during insertion into a human orifice, the device comprising:
a rotatable shaft, wherein the shaft comprises a swab at a distal portion thereof having a plurality of pinwheeling fins each of which has an angled leading edge oriented to collect the biological sample when the shaft is rotated in a pre-selected direction;
wherein the swab contains a channel into which the shaft is inserted, wherein the swab is separable from the shaft by pulling the swab tip away from the shaft.

18. The device according to claim 17, wherein the pinwheeling fins have channels therebetween, wherein the biological sample is collected within said channels when the shaft is rotated in the pre-selected direction.

19. The device according to claim 17, wherein the swab is configured to change colour upon collection of a sample.

20. The device according to claim 17, wherein the swab comprises a dye under the surface of the swab tip.

21. The device according to claim 17, wherein the swab is coated with a pH sensitive solution, reagent, or material.

22. A kit for collection of a biological specimen comprising:
a container for storing the contents of the kit during the transportation thereof, said container having an upper portion attached to a lower portion, which together define an interior space; and
a device according to claim 1 for collection of a biological sample; and
a means of providing user information that uniquely identifies the user; and
a tray attached to the lower portion of the container, said tray having a recess for securely holding the device, wherein the lower portion of the container is configured to provide a base supporting the tray when the container is opened.

23. The kit according to claim 22, which additionally comprises a vessel for preserving and storing the biological specimen once collected.

24. The kit according to claim 23, wherein the tray comprises a recess for securely holding the vessel.

25. The kit according to claim 24, wherein the tray comprises an indentation configured to receive and hold the vessel upright.

26. The kit according to claim 22, which additionally comprises an envelope or container for returning either the device or the vessel by mail.

27. The kit according to claim 26, in which the envelope or container contains a preservative or other means of preventing specimen degradation.

28. The kit according to claim 27, wherein said means of preventing specimen degradation is a coating applied to the interior of the envelope or container.

29. The kit according to claim 22, in which the tray top of the tray is covered by a thin removable expanse, said expanse being removable in separate parts, said separate parts being sequentially numbered so that they can be removed in a pre-determined order, said order being one which allows sequential removal and use of components from the tray.

30. The kit according to claim 22, in which the area of the kit is defined by a maximum length of 300 mm, a maximum width of 200 mm, and a maximum thickness of 20 mm.

* * * * *